United States Patent
Harwell

(10) Patent No.: US 6,825,151 B2
(45) Date of Patent: Nov. 30, 2004

(54) LIQUID HERBICIDAL COMPOSITIONS AND USE THEREOF IN A GRANULAR HERBICIDE

(75) Inventor: Conrad T. Harwell, Lowell, IN (US)

(73) Assignee: Nufarm Americas Inc., Burr Ridge, IL (US)

( * ) Notice: Subject to any disclaimer, the term of this patent is extended or adjusted under 35 U.S.C. 154(b) by 0 days.

(21) Appl. No.: 10/420,298

(22) Filed: Apr. 22, 2003

(65) Prior Publication Data

US 2003/0211943 A1 Nov. 13, 2003

Related U.S. Application Data

(63) Continuation-in-part of application No. 10/060,540, filed on Jan. 30, 2002, now Pat. No. 6,579,831.

(51) Int. Cl.⁷ .................... A01N 43/02; A01N 37/00; A01N 37/08; A01N 37/10
(52) U.S. Cl. ................. 504/127; 504/116.1; 504/128; 504/130; 504/135; 504/142; 504/144; 504/145; 504/146; 504/147
(58) Field of Search ............... 504/116.1, 127, 504/128, 130, 135, 140, 142, 144, 145, 146, 147

(56) References Cited

U.S. PATENT DOCUMENTS

| | | |
|---|---|---|
| 3,637,366 A | 1/1972 | Wietelmann et al. |
| 4,015,970 A | 4/1977 | Hennart |
| 4,213,776 A | 7/1980 | Gülck et al. |
| 5,223,016 A | 6/1993 | Takematsu et al. |
| 5,374,603 A | 12/1994 | Mulqueen et al. |
| 5,436,223 A | 7/1995 | Mulqueen et al. |
| 5,965,487 A | 10/1999 | Flahive |
| 6,022,829 A | 2/2000 | Mito |
| 6,110,866 A | 8/2000 | Walker |
| 6,165,939 A | 12/2000 | Agbaje et al. |
| 6,225,259 B1 * | 5/2001 | Berghaus et al. .......... 504/138 |
| 6,297,197 B1 | 10/2001 | Fields et al. |

FOREIGN PATENT DOCUMENTS

| | | |
|---|---|---|
| GB | 2267825 | * 12/1993 |
| JP | 69013491 | 8/1965 |
| JP | 69123102 | 6/1987 |

* cited by examiner

Primary Examiner—Alton Pryor
(74) Attorney, Agent, or Firm—Marshall, Gerstein & Borun LLP

(57) ABSTRACT

A concentrated, liquid herbicidal composition containing a low volatile ester of a first herbicide, a solid second herbicide comprising fluroxypyr in the form of a free acid and/or a solid ester, and an aprotic solvent is disclosed. A granular herbicide containing a solid substrate having the concentrated, liquid herbicidal composition applied to the substrate also is disclosed.

26 Claims, No Drawings

LIQUID HERBICIDAL COMPOSITIONS AND USE THEREOF IN A GRANULAR HERBICIDE

CROSS-REFERENCE TO RELATED APPLICATIONS

This is a continuation-in-part of U.S. patent application Ser. No. 10/060,540, filed Jan. 30, 2002, now U.S. Pat. No. 6,579,831.

FIELD OF THE INVENTION

The present invention relates to concentrated, liquid herbicidal compositions and the use thereof in a granular herbicide. More particularly, the present invention relates to a liquid herbicidal composition comprising (a) a first herbicide having an acid functionality in the form of a low volatile ester, (b) a solid second herbicide comprising (i) fluroxypyr in the form of a free acid and/or as a solid ester and, optionally, (ii) an herbicide having an acid functionality in the form of a free acid, and (c) an aprotic solvent. The herbicidal composition is applied to a solid substrate to provide a granular herbicide. The substrate comprises an inert material, like a clay, a fertilizer material, or a mixture thereof.

BACKGROUND OF THE INVENTION

Granular herbicides are important commercial products because of their ability to eliminate undesirable vegetation and their ease of application, either by hand or mechanical means. The granular herbicide can be an herbicide applied to an inert material, like clay or ground corn cobs, or can be a combination fertilizer/herbicide, wherein the herbicide is applied to a fertilizer material, i.e., a "weed and feed" composition.

In a granular form, an herbicide is impregnated into or absorbed onto an inert material or a fertilizer material. In the granular form, the herbicide product is supplied in a plastic bag, a plastic drum, or a fiber keg. The granular herbicide product is applied to vegetation by directly spreading the herbicide impregnated granules onto the vegetation at a suitable dosage rate.

It is known that certain compounds, like substituted benzoic acid herbicides and phenoxy-substituted carboxylic acid herbicides, possess selective herbicidal activity against broadleaf vegetation at dosages as low as a few ounces of active herbicide per acre. Accordingly, such herbicides are especially useful in eliminating unwanted vegetation from ornamental turf.

Solid substituted benzoic acid and the phenoxy-substituted carboxylic acid herbicides, and other solid herbicides having a carboxylic acid functionality in a free acid form or an ester form have been applied to susceptible vegetation, but herbicidal effectiveness is relatively poor because the water-insoluble form of these solid herbicides does not sufficiently penetrate the leaves of susceptible vegetation for fast and efficient eradication. In addition, application of such herbicides to a solid substrate is difficult because the free acid form and certain ester forms are solids. Therefore, the solid free acid and ester forms of these herbicides either must be applied to a solid substrate from a solution, which requires solvent removal or absorption of the solvent onto an adsorbent and/or drying agent to provide a dry granular herbicide. Alternatively, to avoid solvents, the solid forms of the herbicide must be applied as either a very finely ground powder or a melt, which requires an expensive heating step and more complex grinding, heating, and application apparatus and processes.

To improve performance, the substituted benzoic acid herbicides and the phenoxy-substituted carboxylic acid herbicides, and other solid herbicidal compounds having an acid functionality, traditionally are converted from the free acid form to a liquid ester form or to a salt form. The salt and liquid ester forms have enhanced water solubility and leaf penetration properties. Both the liquid ester form and the salt form of these herbicidal compounds are available commercially, and are provided as liquid products containing a known, but variable, amount of the active herbicide. For concentrated products, a predetermined amount of water is added to dilute the active herbicide before spraying susceptible vegetation. The predetermined amount of water is related to the concentration of the active herbicide in the liquid herbicidal product and the desired strength of the spraying solution.

In general, the ester forms of these herbicides are provided as petroleum distillate-based emulsifiable concentrates that are diluted with water. The resulting herbicide emulsion then is sprayed on the vegetation to be controlled.

For reasons of economy and safety to the environment and the herbicide applicator, the salt forms of an herbicide often are the preferred form of these herbicides. The salt forms of these herbicides are provided as concentrated aqueous solutions that are diluted with water. However, some water-soluble, solid forms of the salt form of these herbicidal compounds also are available. The solid forms typically are water-soluble, solid products containing essentially only the herbicide (see Champion et al. U.S. Pat. No. 5,266,553), as opposed to water-insoluble granular products. Also, see Flahine U.S. Pat. No. 5,965,487, and Mulqueen et al. U.S. Pat. Nos. 5,374,603 and 5,436,223.

In addition, granule herbicides are prepared by impregnating a substrate with a highly concentrated aqueous solution of the herbicide salt, which often requires the addition of expensive drying agents, such a corn cob granules or silica, in order to provide a noncaking, dry granular herbicide. The highly concentrated aqueous solution of the herbicide salt used to make the granule herbicide tend to form crystals when stored at relatively cool temperatures, i.e., at temperatures below 40° F. Because the majority of granular herbicide manufacturing is done during the winter months, special heating and mixing of the aqueous herbicide concentrates prior to application onto the substrate is necessary to assure that the substrate is impregnated with the precise loading required by U.S. federal regulations.

The ester and salt forms of herbicides containing an acid functionality traditionally are applied to solid substrates, but suffer in cost and difficulty of manufacture because of the previously mentioned problems of solvent removal, and the need to utilize expensive drying agents. In addition, applying a salt form of the herbicide to a substrate often is not practical or feasible. First, applying an aqueous solution of the salt form of an herbicide to a water-soluble substrate wets substrate surfaces and makes processing difficult. Second, a solid salt form of an herbicide is difficult to apply, and especially to apply evenly, to a solid substrate. In addition, granular herbicides manufactured by adding a solid salt form of an herbicide to a substrate are hygroscopic, which causes clumping and stickiness, and requires addition of a drying agent to the composition.

Therefore, it would be advantageous to provide a highly concentrated, liquid herbicidal composition that can be applied directly to a solid substrate, without dilution or addition of drying agents, to provide a granular herbicide containing the desired herbicide combination in the desired amounts. The concentrated liquid herbicidal composition avoids the need to apply an herbicide solution or a molten herbicide to a substrate, which reduces manufacturing costs and equipment associated with preparing an herbicide solution or melting a solid herbicide, applying the molten herbicide to a solid substrate, and evaporating solvent. It also would be advantageous to provide a concentrated liquid herbicidal composition that exhibits excellent cold storage stability, and can be applied at relatively cool temperatures, compared to present-day herbicidal compositions applied to a granular substrate.

SUMMARY OF THE INVENTION

The present invention is directed to concentrated, liquid herbicidal compositions. The concentrated herbicidal compositions are used in undiluted form to prepare granular herbicides.

More particularly, the present invention is directed to a concentrated, liquid herbicidal composition comprising (a) a first herbicide having an acid functionality in the form of a low volatile ester, (b) a solid second herbicide comprising (i) fluroxypyr in the form of a free acid and/or as a solid ester, and, optionally, (ii) an herbicide having an acid functionality in the form of a free acid, and (c) an aprotic solvent. The composition comprises about 55% to about 85%, by weight, of the first herbicide, about 6% to about 35%, by weight, of the solid second herbicide, and about 1% to about 10%, by weight, of the aprotic solvent.

As used herein, the term "acid functionality" is defined to include a carboxylic acid functionality ($CO_2H$) and a phenolic functionality (OH).

The term "solid ester form" is defined as an ester of fluroxypyr, or an ester of other carboxylic acid containing herbicides, having a melting point of greater than 25° C. at 760 mm pressure.

The concentrated herbicidal composition is used in the manufacture of a granular herbicide. As used herein, the term "granular herbicide" is defined as an herbicide or mixture of herbicides absorbed, impregnated, or coated onto a solid substrate. The solid substrate can be an inert material, e.g., a clay, and/or can be a fertilizer material, e.g., urea/formaldehyde fertilizers, urea, potassium chloride, ammonium compounds, phosphorus compounds, sulfur, similar plant nutrients and micronutrients, and mixtures and combinations thereof, both synthetic and naturally occurring organic and inorganic materials.

Therefore, one aspect of the present invention is to provide a highly concentrated, liquid herbicidal composition. Another aspect of the present invention is to utilize the herbicidal composition, without dilution, in the preparation of a granular herbicide.

Yet another aspect of the present invention is to provide a liquid herbicidal composition consisting essentially of the first herbicide, the solid second herbicide, and the aprotic solvent, in the form of a homogeneous liquid. The herbicidal composition is free, or at least essentially free, of a protic solvent, such as an alcohol or a glycol. The absence of a protic solvent prevents the undesirable formation of esters of the solid second herbicide.

Another aspect of the present invention is to provide a method of preparing a granular herbicide comprising the step of applying the undiluted herbicidal composition to the surfaces of a solid substrate. The method optionally comprises a step of heating the herbicidal composition at a temperature of about 80° F. to about 100° F. to improve the flow and spray properties of the herbicidal composition, and thereby facilitate application of the herbicidal composition to the substrate, as opposed to solubilizing a solid present in the herbicidal composition.

Yet another aspect of the present invention is to provide a liquid herbicidal composition comprising (a) a first herbicide (low volatile ester form), (b) a solid second herbicide comprising (i) fluroxypyr in the form of a free acid and/or as a solid ester, and optionally, (ii) an herbicide having an acid functionality free acid form independently selected from (a) a substituted benzoic acid herbicide, especially methoxy-substituted or halogen-substituted benzoic acid herbicides; (b) a phenoxy-substituted carboxylic acid herbicide, especially chlorophenoxy-substituted carboxylic acid herbicides; (c) herbicides having a nitrogen-containing heterocyclic ring and a carboxylic acid functionality, especially substituted picolinic acid and pyridine containing herbicides; and (d) miscellaneous herbicides having an acid functionality. The first, second, and optional herbicides, independently, can be, for example, triclopyr, clopyralid, 2,4-dichlorophenoxyacetic acid (2,4-D), 2-(2,4-di-chlorophenoxy)propionic acid (2,4-DP), 2,4-dichlorophenoxybutyric acid (2,4-DB), 2-methyl-4-chlorophenoxyacetic acid (MCPA), 2-(2-methyl-4-chlorophenoxy)-propionic acid (MCPP), 2-methyl-4-chlorophenoxy-butyric acid (MCPB), endothall, glufosinate, glyphosate, picloram, bromoxynil, carfentrazone, and mixtures thereof. At least a portion of the second herbicide comprises fluroxypyr, in the form of a free acid or a solid ester.

The above and other aspects and advantages of the present invention will become apparent from the following detailed description of the preferred embodiments.

DETAILED DESCRIPTION OF THE PREFERRED EMBODIMENTS

A concentrated, liquid herbicidal composition of the present invention comprises (a) about 55% to about 85%, by weight, of a first herbicide having an acid functionality in the low volatile ester form, (b) about 6% to about 35%, by weight, of a solid second herbicide comprising fluroxypyr in the form of a free acid and/or as a solid ester, and optionally, an herbicide having an acid functionality in the free acid form, and (c) about 1% to about 10%, by weight, of an aprotic solvent. The concentrated herbicidal composition is used in the manufacture of a granular herbicide by applying the herbicidal composition to surfaces of a solid substrate. The solid substrate can be an inert material, can comprise one or more fertilizer materials, or a mixture of inert materials and fertilizer materials.

In preferred embodiments, the first herbicide is present in an amount of about 57% to about 75%, by weight, and the second herbicide is present in an amount of about 10% to about 30%, by weight, of the composition. To achieve the full advantage of the present invention, the first and second herbicides are present in amounts of about 60% to about 70%, and about 12% to about 25%, by weight, of the composition, respectively.

In accordance with an important feature of the present invention, the first herbicide has an acid functionality that has been converted to a low volatile ester. A "low volatile ester" is known in the art as an ester form of a herbicide prepared by esterifying an acid functionality of the herbicide with an alcohol containing six to ten carbon atoms, and preferably six to eight carbon atoms. The alcohol can further contain oxygen atoms to provide ether linkages. Typical alcohols used to prepare a low volatile ester of an herbicide include, but are not limited to, decyl alcohol, octyl alcohol, heptyl alcohol, 2-butoxyethanol, butoxypropanol, and 2-ethylhexyl alcohol. The first herbicide has sufficient solvency to dissolve the solid second herbicide, without the formation of a precipitate even when stored at cold temperatures (i.e., 10° F. and above).

In accordance with another important feature of the present invention, the second herbicide is a solid. The second herbicide comprises fluroxypyr in the form of a solid ester, in the form of a free acid, i.e., in the $CO_2H$ form for a carboxylic acid, or a mixture thereof. The second herbicide also, optionally, can contain a solid herbicide in the free acid form, i.e., the acid functionality is in the $Co_2H$ form for a carboxylic acid or the OH form for a phenol. Both the first herbicide and second herbicide can be based on the same herbicide, e.g., fluroxypyr, but in this case the first fluroxypyr herbicide is in the form of a liquid ester and the second fluroxypyr herbicide is in the form of a solid ester, in the free acid form, or a mixture thereof. Typically, the first and second herbicide are different herbicides, e.g., 2,4-D ester as the first herbicide and fluroxypyr as the second herbicide.

In addition, the first herbicide either can be a single herbicide in the low volatile ester form or can be a mixture of herbicides in the low volatile ester form. Similarly, the solid second herbicide either can be a single herbicide in the solid ester or free acid form (i.e., fluroxypyr) or can be a mixture of solid herbicides in the solid ester or free acid form (i.e., fluroxypyr and an optional second herbicide).

As previously stated, both the first and second herbicide have an acid functionality, and can be independently selected from herbicides such as, for example, (a) substituted benzoic acid herbicides, (b) phenoxy-substituted carboxylic acid herbicides, (c) herbicides having a nitrogen-containing heterocyclic ring and a carboxylic acid functionality, and (d) miscellaneous herbicides having a carboxylic acid functionality or phenolic functionality. Specific examples of herbicides useful as first and/or second herbicides include, but are not limited to: (a) substituted benzoic acid herbicides including, but not limited to, 2-methoxy-3,6-dichlorobenzoic acid (dicamba), 2,3,6-trichlorobenzoic acid, 3,5,6-trichloro-o-anisic acid (tricamba), 3-amino-2,5-dichlorobenzoic acid (amiben), 5-2-[2-chloro-4-(trifluoromethyl)phenyoxy]-2-nitrobenzoic acid (acid form of acifluorfen), and 2,3,5-triiodobenzoic acid; (b) phenoxy-substituted carboxylic acid herbicides, including, but not limited to: 2,4-dichlorophenoxyacetic acid (2,4-D), 2,4-dichlorophenoxybutyric acid (2,4-DB), 2-(2,4-dichlorophenoxy)propionic acid (2,4-DP), 2,4,5-trichlorophenoxyacetic acid (2,4,5-T), 2-(2,4,5-trichlorophenoxy)butyric acid, 2-(2,4,5-trichlorophenoxy)propionic acid (silvex), 4-chloro-2-methylphenoxyacetic acid (MCPA), 2-(4-chloro-2-methylphenoxy)propionic acid (MCPP), 4-(4-chloro-2-methylphenoxy)butyric acid (MCPD), and 2-[4-(2',4'-dichlorophenoxy)phenoxy] propanoic acid (diclofop); and (c) herbicides having a nitrogen-containing heterocyclic ring and a carboxylic acid functionality, and miscellaneous herbicidal compounds having a carboxylic acid functionality, including, but not limited to: fluroxypyr, carfentrazone, 2,2-dichloropropionic acid (dalapon), 2,2,3-trichloropropionic acid, 7-oxabicyclo [2.2.1]heptane-2,3-dicarboxylic acid (endothall), (2,3,6-trichlorophenyl)acetic acid (fenac), glufosinate, gallic acid, gibberellic acid, trichloroacetic acid, β-naphthoxyacetic acid, N -(phosphonomethyl)glycine (glyphosate), 4-amino-3,5,6-trichloropicolinic acid (picloram), 3,6-dichloropicolinic acid (clopyralid), 3,5,6-trichloro-2-pyridinyloxyacetic acid (triclopyr), and 9-undecylenic acid, and bromoxynil.

A preferred first herbicide is a phenoxy-substituted carboxylic acid, especially an herbicide selected from the group consisting of 2,4-D, 2,4-DB, MCPP, MCPA, bromxynil, carfentrazone, and mixtures thereof. The preferred ester of the first herbicide is a 2-ethylhexyl ester or a 2-butoxyethyl ester. To achieve the full advantage of the present invention, the first herbicide comprises the 2-ethylhexyl ester of 2,4-D.

The solid second herbicide comprises fluroxypyr either in form of a solid ester and/or in the free acid form. Fluroxypyr also is known as 4-amino-3,5-dichloro-6-fluoro-2-pyridyloxyacetic acid. Solid ester forms of fluroxypyr useful in the present invention include, but are not limited to, the methylheptyl ester (meptyl) and the methyl ester. The fluroxypyr component of the second herbicide comprises about 50% to 100%, and preferably about 75% to 100%, by weight of the second herbicide.

A preferred optional second herbicide is selected from the group consisting of 2,4-D, MCPP, MCPA, 2,4-DB, dicamba, picloram, clopyralid, triclopyr, bromoxynil, carfentrazone, and mixtures thereof. To achieve the full advantage of the present invention, the optional second herbicide is selected from the group consisting of 2,4-D, MCPP, MCPA, dicamba, clopyralid, triclopyr, carfentrazone, bromoxynil, and mixtures thereof. The optional second herbicide comprises 0% to about 50%, and preferably 0% to about 25%, by weight, of the second herbicide.

In preferred embodiments, the concentrated herbicidal composition contains the aprotic solvent in an amount of about 1.5% to about 8%, by weight of the composition. To achieve the full advantage of the present invention, the herbicidal composition contains about 2.5% to about 6% of the aprotic solvent, by weight of the composition.

The amount of aprotic solvent included in a particular herbicidal composition is related to the amount and identity of the first and second herbicide in the composition. In particular, the aprotic solvent is present in a sufficient amount to provide an herbicidal composition that is a clear solution at room temperature, i.e., 70° F., or under mild heating conditions, i.e., heating to a maximum of 100° F., and preferably to about 80° F. to about 85° F. For compositions that require slight heating to provide a clear solution, a sufficient amount of the aprotic solvent is present to provide a composition of the present invention that is a flowable viscous liquid or semisolid at room temperature and does not require heating to apply the herbicidal composition to a solid substrate. The aprotic solvent also is present in a sufficient amount to prevent the solid second herbicide from precipitating from the composition.

The aprotic solvent is free of hydroxyl groups. The presence of hydroxyl groups is avoided because a solvent containing hydroxyl groups can esterify the second herbicide and change the chemical makeup of the composition. In particular, herbicides are highly regulated products, and the composition must conform to label specifications. Therefore, esterification and/or transesterification of the second herbicide must be avoided in order to conform to label specifications. The aprotic solvent also is nonreactive, has a high solvency, has a relatively high boiling point (e.g., about 200° F. to about 350° F.) to avoid premature evaporation, and has a low odor for consumer acceptance.

Accordingly, an herbicidal composition of the present invention is free, or at least essentially free, of an alcohol. The term "essentially free of an alcohol" is defined as a composition wherein no alcohol is added intentionally to the composition. However, an alcohol can be present in the composition as a by-product or inert ingredient of a component in composition. For example, the first herbicide may contain a low percentage of unreacted alcohol from the esterification reaction required to form the first herbicide. Alternatively stated, as used herein, the term "essentially free of an alcohol" is defined as a composition containing less than 2%, typically less than 0.5%, and down to zero percent, of an alcohol.

In particular, the aprotic solvent can be, but is not limited to, N-methyl-pyrrolidone (NMP), dimethyl sulfoxide (DMSO), γ-butyrolactone, dimethylformamide (DMF), hexamethylphosphoramide (HMPA), cyclohexanone, aromatic solvents (e.g., benzene, toluene, xylene, ethylbenzene, and similar aromatic solvents), and mixtures thereof.

A concentrated herbicidal composition of the present invention can be prepared by simply admixing the solid second herbicide containing fluroxypyr with the liquid first herbicide and a sufficient amount of the aprotic solvent to provide a liquid, concentrated herbicidal composition of the present invention. The relative order of addition is not critical, e.g., the aprotic solvent can be added to the composition before or after the second herbicide is added to the first herbicide.

The effect of incorporating an aprotic solvent, e.g., NMP or an aromatic solvent, into a herbicidal composition is demonstrated by the following test. In particular, three formulations containing the 2-ethylhexyl ester of 2,4-D as the first herbicide and a mixture of MCPP and dicamba as the second herbicide were prepared. NMP is present in the individual formulations in amounts of 0%, 2.91%, or 5%, by weight.

| Herbicide | Wt. %[1] | Purity %[2] | Actives[3] | Herbicide Ratio (as acid) |
|---|---|---|---|---|
| 2-Ethylhexyl ester of 2,4-D (first herbicide) | 66.16 | 95 (as ester) 63 (as acid equivalent) | 62.85 (as ester) 41.68 (as acid equivalent) | 12.5 |
| MCPP-p acid (second herbicide) | 27.18 | 92 | 25.01 | 7.5 |
| DICAMBA acid (2nd herbicide) | 3.75 | 89 | 3.34 | 1 |
| NMP | 2.91 | 100 | | |
| Total | 100 | | 70.03 (as acid equivalent) | |

[1] weight % in the composition on an "as is" basis, which includes the amount of any inert ingredients present in the component;
[2] the purity of each component as added to the composition, and
[3] the amount of each herbicide component in the formulation based on the ester form and/or acid form of the herbicide.

Similar compositions having a 12.5:7.5:1 weight ratio of herbicides, but containing either 0% or 5%, by weight, NMP also were prepared.

The composition containing 5% NMP was a clear solution, both immediately after manufacture and after three months storage at room temperature. The composition containing 0% NMP solidified into a stiff gel after a short storage time at room temperature. The composition containing 2.91% NMP was a clear solution after manufacture, but formed a soft, opaque, flowable semisolid after storage for three months. This semisolid was pumpable and could be applied in an undiluted form to a solid substrate to provide a granular herbicide. To facilitate application to a solid substrate, this semisolid could be heated at about 80° F. for a short time to provide a clear solution.

The following are additional examples of the present invention.

EXAMPLE 1

| Ingredient | Wt. %[1] | Purity %[2] | Actives[3] | Ratio (as acid) |
|---|---|---|---|---|
| 2,4-D, 2-ethylhexyl ester (first herbicide) | 68.55 | 95 (as ester) 63 (as acid equivalent) | 65.12 (as ester) 43.34 (as acid equivalent) | 5 (1.666) |
| MCPP-p (second herbicide) | 28.22 | 92 | 26 | 3 (1.000) |
| NMP | 3.22 | 100 | | |
| Total | 100 | | 69.34 (as acid equivalent) | |

The composition of Example 1 was a clear solution, and remained a clear liquid after storage at room temperature for three months.

EXAMPLE 2

| Ingredient | Wt. %[1] | Ratio (as acid) |
|---|---|---|
| 2,4-D, 2-ethylhexyl ester (first herbicide) | 86.13 | |
| 2,4-D, acid (second herbicide) | 7.21 | 25 (total 2,4-D as acid) |
| LONTREL[4] (second herbicide) | 3.01 | 1 |
| Dicamba (second herbicide) | 2.74 | 1 |
| NMP | 0.91 | |
| Total | 100 | |

[4] clopyralid (about 78% active)

EXAMPLE 3

| Ingredient | Wt. %[1] | Ratio (as acid) |
|---|---|---|
| 2,4-D, 2-ethylhexyl ester (first herbicide) | 89.19 | 20.8 |
| LONTREL[4] (second herbicide) | 3.44 | 1 |
| Dicamba (second herbicide) | 3.03 | 1 |
| NMP | 4.34 | |
| Total | 100 | |

EXAMPLE 4

| Ingredient | Wt. %[1] | Wt % (as acid equivalent) | Ratio (as acid) |
|---|---|---|---|
| 2,4-D, 2-ethylhexyl ester[5] (first herbicide) | 74.54 | 46.96 | 10 |

-continued

| Ingredient | Wt %[1] | Wt % (as acid equivalent) | Ratio (as acid) |
|---|---|---|---|
| Fluroxypyr methylheptyl ester[6] (second herbicide) | 17.25 | 11.73 | 2.5 |
| Trichlopyr[7] (second herbicide) | 6.76 | 4.7 | 1 |
| Aromatic 150 Solvent | 1.45 | | |
| Total | 100 | | |

[5] about 63%, by weight, active, as acid
[6] about 68%, by weight, active, as ester
[7] about 69.5%, by weight, active, as acid

EXAMPLE 5

| Ingredient | Wt %[1] | Wt % (as acid equivalent) | Ratio (as acid) |
|---|---|---|---|
| 2,4-D, 2-ethylhexyl ester[5] (first herbicide) | 73.34 | 46.20 | 8 |
| Fluroxypyr methylheptyl ester[6] (second herbicide) | 16.99 | 11.55 | 2 |
| Dicamba[8] (second herbicide) | 6.49 | 5.78 | 1 |
| Aromatic 150 Solvent | 3.18 | | |
| Total | 100 | | |

[8] about 89%, by weight, active, as acid

EXAMPLE 6

| Ingredient | Wt %[1] | Wt % (as acid equivalent) | Ratio (as acid) |
|---|---|---|---|
| 2,4-D, 2-ethylhexyl ester[5] (first herbicide) | 84.30 | 52.63 | 20 |
| Fluroxypyr methylheptyl ester[6] (second herbicide) | 9.76 | 6.58 | 2.5 |
| Trichlopyr[7] (second herbicide) | 2.94 | 2.63 | 1 |
| Aromatic 150 Solvent | 3.00 | | |
| Total | 100 | | |

EXAMPLE 7

| Ingredient | Wt %[1] | Wt % (as acid equivalent) | Ratio (as acid) |
|---|---|---|---|
| 2,4-D, 2-ethylhexyl ester[5] (first herbicide) | 83.74 | 52.76 | 16 |
| Fluroxypyr methylheptyl ester[6] (second herbicide) | 9.69 | 6.60 | 2 |
| Dicamba[8] (second herbicide) | 3.70 | 3.30 | 1 |
| Aromatic 150 Solvent | 2.86 | | |
| Total | 100 | | |

A concentrated herbicidal composition of the present invention is used in the manufacture of granular herbicides. In particular, a present herbicidal composition is applied to a solid substrate in a sufficient amount to provide a granular herbicide of a predetermined herbicidal strength. The herbicidal concentrate is applied to the solid substrate by any method known to persons skilled in the art, and typically by spraying the herbicidal concentrate onto surfaces of the solid substrate accompanied by mixing of the solid substrate. In accordance with an important feature of the present invention, the herbicidal composition is a pumpable and sprayable composition and is applied without dilution.

The solid substrate of the granular herbicide can be an inert material, a fertilizer material, or a mixture thereof. As used herein, the term "fertilizer material" is defined as any substance capable of supplying plant nutrients, e.g., primary, secondary, and/or micronutrients, to vegetation.

The solid substrate particles typically have a major diameter of about 0.6 to about 16 mm, more preferably about 1 to about 8 mm. The total weight of the undiluted herbicidal composition applied to the solid substrate typically is about 3% to about 20% of the total weight of the granular herbicide.

Inert materials that can be used as the solid substrate include, but are not limited to, dried clay, calcium carbonate, brick, pumice, pyrophyllite, sulphur, kaolin, dolomite, plaster, wood flour, ground corn cobs, sugars, sodium chloride, sodium sulfate, sodium silicate, sodium borate, magnesia, mica, iron oxide, zinc oxide, titanium oxide, antimony oxide, cryolite, vermiculite calcinated lime, gypsum, perlite, diatomaceous earth, bentonite clay, calcium sulfate, and mixtures thereof.

Fertilizer materials that can be used as the solid substrate include, but are not limited to, water-soluble and water-insoluble materials, like ammonium sulfate, ammonium chloride, ammonium nitrate, an ammonium phosphate, sodium nitrate, potassium nitrate, calcium nitrate, potassium chloride, potassium sulfate, potassium carbonate, a sodium phosphate, a potassium phosphate, urea, compounds capable of providing vegetation a micronutrient, such as copper, magnesium, zinc, calcium, boron, molybdenum, manganese, iron, and nickel, such as magnesium sulfate, an iron chelate, manganese sulfate, nickel sulfate, zinc sulfate, copper sulfate, animal dung fertilizers, MILORGANITE and HOUACTINITE organic fertilizers, and mixtures thereof.

The granular herbicide and the concentrated herbicidal composition also can contain various optional ingredients known to persons skilled in the art. For example, adjuvants, de-dusting agents, other pesticides (e.g., insecticides or growth regulators), stabilizers, surfactants, dyes, and similar optional ingredients can be included to provide granular herbicides that are safely handled and convenient to apply accurately to areas in need of treatment. The granular herbicide is applied in an amount sufficient to assure herbicidal action. The amount applied depends on the herbicide in the herbicidal composition and the purpose for which it is being used.

A granular herbicide of the present invention is prepared as follows. When the substrate is an inert material or a single fertilizer material, the substrate is provided in a suitable size and optional ingredients can be added. If the substrate is a blend of fertilizer materials, or a fertilizer material blended with an inert material, the solid substrate first is prepared by methods known in the art, e.g., blending. In either case, the solid substrate first is provided, then the herbicidal composition then is applied to the solid substrate.

For example, a large drum-shaped vessel capable of holding a dry, solid substrate, and able to rotate at an inclined angle along the center axis, can be used. The components of the solid substrate are added to the drum during rotation to facilitate a mixing or blending action. Typically, the vessel has means for spraying a liquid herbicidal composition onto the solid substrate. Spraying serves to impregnate or coat the surfaces of the solid substrate with the liquid herbicidal composition. Often the method of incorporating the herbicidal composition onto the solid substrate involves the use of a pump and nozzles to propel small droplets of the herbicidal composition onto the solid substrate such that the herbicidal composition is evenly distributed on the solid substrate. Optionally, during the process of mixing, a small amount of an additive, such as a nonionic surfactant, can be sprayed onto the solid substrate to facilitate formation of a uniform coating on the particles of the solid substrate.

By using different amounts of a given fertilizer material, a desired level and ratio of nitrogen, phosphorus, and potassium, also known as the NPK value, can be achieved. For example, to produce a ton of a fertilizer containing an NPK value of 16-16-18 requires mixing of 700 pounds urea, 700 pounds super triple phosphate, and 600 pounds of coarse potash. This fertilizer material has an NPK composition, plus sulfur, of 22-4-12+7S, and can be used as the solid substrate of the granular herbicide.

After the fertilizer material is prepared, the undiluted, concentrated herbicidal composition is sprayed onto the dry fertilizer material. The herbicidal composition is sprayed utilizing a pump to pressurize the herbicidal composition and nozzles to control and direct the herbicidal composition spray. The herbicidal composition is applied, undiluted, in an amount of about 1% to about 20%, and typically about 1% to about 10%, by weight, of the granular herbicide. If the fertilizer material becomes damp or wet during addition of the herbicidal composition, and is difficult to manage, drying agents, such as clay, calcium sulfate, corn cob, silica powders, or vermiculite can be added in an amount of about 3 to about 50 pounds per ton of fertilizer material to facilitate manufacture of the granular herbicidal.

EXAMPLE 8

| Ingredient | (A) Wt. % | (B) Wt. % |
|---|---|---|
| Example 4 | 1.53 | 1.23 |
| Solid fertilizer material (NPK) | 98.47 | 98.77 |
| Total | 100 | |

NPK is nitrogen, phosphorus, and potassium.

EXAMPLE 9

| Ingredient | Wt. % |
|---|---|
| Example 4 | 1.55 |
| Solid fertilizer material (NPK) | 98.25 |
| HI-SIL 233 Silica[9] | 0.20 |
| Total | 100 |

[9]Available from PPG Industries, Pittsburgh, PA.

EXAMPLE 10

| Ingredient | (A) Wt. % | (B) Wt. % |
|---|---|---|
| Exzample 5 | 1.24 | 2.80 |
| Solid fertilizer material (NPK) | 98.76 | 96.20 |
| HI-SIL 233 Silica[9] | | 1.00 |
| Total | 100 | 100 |

EXAMPLE 11

| Ingredient | Wt. % |
|---|---|
| Example 6 | 96.99 |
| Solid fertilizer material (NPK) | 2.81 |
| HI-SIL 233 Silica[9] | 0.20 |
| Total | 100 |

Many modifications and variations of the invention as hereinbefore set forth can be made without departing from the spirit and scope thereof and, therefore, only such limitations should be imposed as are indicated by the appended claims.

What is claimed is:

1. A composition consisting essentially of
   (a) about 55% to about 85%, by weight, of a first herbicide having an acid functionality in a form of a low volatile ester prepared from an alcohol containing six to ten carbon atoms;
   (b) about 6% to about 35%, by weight, of a solid second herbicide is fluroxypyr in the form of a free acid, a solid ester, or a mixture thereof, and, optionally, a herbicide having a acid functionality in a form of a free acid; and
   (c) about 1% to about 10%, by weight, of an aprotic solvent.

2. The composition of claim 1 wherein the first herbicide is present in an amount of about 57% to about 75%, by weight.

3. The composition of claim 1 wherein the first herbicide is present in an amount of about 60% to about 70%, by weight.

4. The composition of claim 1 wherein the solid second herbicide is present in an amount of about 10% to about 30%, by weight.

5. The composition of claim 1 wherein the solid second herbicide is present in an amount of about 12% to about 25%, by weight.

6. The composition of claim 1 wherein the second herbicide is fluroxypyr in the form of a free acid, a solid ester, or a mixture thereof, in an amount of about 50% to 100%, by weight, of the second herbicide.

7. The composition of claim 1 wherein the second herbicide is fluroxypyr in the form of a free acid, a solid ester, or a mixture thereof, in an amount of about 75% to 100%, by weight, of the second herbicide.

8. The composition of claim 1 wherein the fluroxypyr component of the second herbicide comprises the methylheptyl ester of fluroxypyr, the methyl ester of fluroxypyr, the acid form of fluroxypyr, or a mixture thereof.

9. The composition of claim 1 wherein the aprotic solvent is present in an amount of about 1.5% to about 8%, by weight.

10. The composition of claim 1 wherein the aprotic solvent is present in an amount of about 2.5% to about 6%, by weight.

11. The composition of claim 1 wherein the first herbicide comprises a decyl ester, a heptyl ester, an octyl ester, a butoxypropyl ester, a 2-ethylhexyl ester, a 2-butoxyethyl ester, or mixtures thereof.

12. The composition of claim 1 wherein the first herbicide having an acid functionality is selected from the group consisting of a substituted benzoic acid herbicide, a phenoxy-substituted carboxylic acid herbicide, an herbicide having a nitrogen-containing heterocyclic ring and a carboxylic acid functionality, and mixtures thereof.

13. The composition of claim 1 wherein the optional solid second herbicide is selected the group consisting of a substituted benzoic acid herbicide, a phenoxy-substituted carboxylic acid herbicide, an herbicide having a nitrogen-containing heterocyclic ring and a carboxylic acid functionality, and mixtures thereof.

14. The composition of claim 1 wherein the first herbicide and the optional solid second herbicide having an acid functionality, independently, are selected from the group consisting of 2-methoxy-3,6-dichlorobenzoic acid, 2,3,6-trichlorobenzoic acid, 3,5,6-trichloro-o-anisic acid, 3-amino-2,5-dichlorobenzoic acid, 5-2-[2-chloro-4-(trifluoromethyl)phenyoxy]-2-nitrobenzoic acid, 2,3,5-triiodobenzoic acid, 2,4-dichlorophenoxyacetic acid, 2,4-dichlorophenoxybutyric acid, 2-(2,4-dichlorophenoxy)-propionic acid, 2,4,5-trichlorophenoxyacetic acid, 2-(2,4,5-trichlorophenoxy)butyric acid, 2-(2,4,5-trichlorophenoxy) propionic acid, 4-chloro-2-methylphenoxyacetic acid, 2-(4-chloro-2-methylphenoxy)propionic acid, 4-(4-chloro-2-methylphenoxy)butyric acid, 2-[4-(2',4'-dichlorophenoxy) phenoxy]propanoic acid, carfentrazone, 2,2-dichloropropionic acid, 2,2,3-trichloropropionic acid, 7-oxabicyclo[2.2.1]heptane-2,3-dicarboxylic acid, (2,3,6-trichlorophenyl)acetic acid, glufosinate, gallic acid, gibberellic acid, trichloroacetic acid, β-naphthoxyacetic acid, N-(phosphonomethyl)glycine, 4-amino-3,5,6-trichloropicolinic acid, 3,6-dichloropicolinic acid, 3,5,6-trichloro-2-pyridinyloxyacetic acid, 9-undecylenic acid, bromoxynil, and mixtures thereof.

15. The composition of claim 1 wherein the first herbicide is a low volatile ester of a phenoxy-substituted carboxylic acid herbicide.

16. The composition of claim 1 wherein the first herbicide, in the form of a low volatile ester, is selected from the group consisting of 2,4-dichlorophenoxyacetic acid, 2,4-dichlorophenoxybutyric acid, 2-(4-chloro-2-methylphenoxy)propionic acid, MCPA, 2,4-DP, bromoxynil, fluroxypyr, carfentrazone, and mixtures thereof.

17. The composition of claim 1 wherein the optional solid second herbicide having an acid functionality is selected from the group consisting of 2,4-dichlorophenoxyacetic acid, 2,4-dichlorophenoxybutyric acid, 2-(4-chloro-2-methylphenoxy)propionic acid, 4-amino-3,5,6-trichloropicolinic acid, 3,6-dichloropicolinic acid, 3,5,6-trichloro-2-pyridinyloxyacetic acid, 2-methoxy-3,6-dichlorobenzoic acid, bromoxynil, carfentrazone, and mixtures thereof.

18. The composition of claim 1 wherein the aprotic solvent is selected from the group consisting of N-methylpyrrolidone, dimethyl sulfoxide, γ-butyrolactone, dimethylformamide, hexamethylphosphoramide, cyclohexanone, an aromatic solvent, and mixtures thereof.

19. The composition of claim 1 wherein the first herbicide, in the form of a low volatile ester, is selected from the group consisting of 2,4-dichlorophenoxyacetic acid, 2,4-dichlorophenoxybutyric acid, 2-(4-chloro-2-methylphenoxy)propionic acid, fluroxypyr, carfentrazone, bromoxynil, and mixtures thereof; and the second herbicide comprises fluroxypyr in the form of a free acid, a solid ester, or a mixture thereof, and, optionally, 2,4-dichlorophenoxyacetic acid, 2,4-dichlorophenoxybutyric acid, 2-(4-chloro-2-methylphenoxy)propionic acid, 4-amino-3,5,6-trichloropicolinic acid, 3,6-dichloropicolinic acid, 3,5, 6-trichloro-2-pyridinyloxyacetic acid, 2-methoxy-3,6-dichlorobenzoic acid, carfentrazone, bromoxynil, or mixtures thereof.

20. The composition of claim 19 wherein the aprotic solvent comprises an aromatic solvent, N-methylpyrrolidone, or a mixture thereof.

21. The composition of claim 19 wherein the first herbicide is in the form of a 2-ethylhexyl ester or a 2-butoxyethyl ester.

22. The composition of claim 21 wherein the first herbicide is the 2-ethylhexyl ester of 2,4-dichlorophenoxyacetic acid, and the second herbicide is fluroxypyr in the form of a free acid, a solid ester, or a mixture thereof, and, optionally, 2-methoxy-3,6-dichlorobenzoic acid, 2-(4-chloro-2-methylphenoxy)propionic acid, 3,6-dichloropicolinic acid, carfentrazone, bromoxynil, and mixtures thereof.

23. The composition of claim 22 wherein the aprotic solvent comprises an aromatic solvent.

24. A granular herbicide prepared by applying a composition of claim 1, in an undiluted form, to a solid substrate.

25. The granular herbicide of claim 24 wherein the solid substrate comprises an inert material, a fertilizer material, or a mixture thereof.

26. A composition consisting essentially of
   (a) about 55% to about 85%, by weight, of a first herbicide having an acid functionality in a form of a low volatile ester;
   (b) about 6% to about 35%, by weight, of a solid second herbicide comprising fluroxypyr in the form of a free acid, a solid ester, or a mixture thereof, and, optionally, an herbicide having an acid functionality in a form of a free acid; and
   (c) about 1% to about 10%, by weight, of an aprotic solvent.

* * * * *

UNITED STATES PATENT AND TRADEMARK OFFICE
CERTIFICATE OF CORRECTION

PATENT NO. : 6,825,151 B2
DATED : November 30, 2004
INVENTOR(S) : Conrad T. Harwell It is certified that error appears in the above-identified patent and that said Letters Patent is hereby corrected as shown below:

<u>Title page,</u>
Item [*] Notice, please insert -- This patent is subject to a terminal disclaimer. --

<u>Column 12,</u>
Lines 38-39, "a acid" should be -- an acid --

<u>Column 13,</u>
Line 15, "is selected the group" should be -- is selected from the group --

Signed and Sealed this

Seventh Day of June, 2005

JON W. DUDAS
*Director of the United States Patent and Trademark Office*